United States Patent
Dohse et al.

(10) Patent No.: US 10,456,506 B2
(45) Date of Patent: Oct. 29, 2019

(54) PRODUCTION OF RESORBABLE POLYMER TUBES MADE OF THREADS

(71) Applicant: MeKo Laserstrahl-Materialbearbeitungen e.K., Sarstedt (DE)

(72) Inventors: Jakob Dohse, Hannover (DE); Bernd Hinrichs, Sehnde (DE)

(73) Assignee: MEKO LASERSTRAHL-MATERIALBEARBEITUNGEN E.K., Sarstedt (DE)

( * ) Notice: Subject to any disclaimer, the term of this patent is extended or adjusted under 35 U.S.C. 154(b) by 0 days.

(21) Appl. No.: 15/105,466

(22) PCT Filed: Dec. 15, 2014

(86) PCT No.: PCT/EP2014/077754
§ 371 (c)(1),
(2) Date: Jun. 16, 2016

(87) PCT Pub. No.: WO2015/091357
PCT Pub. Date: Jun. 25, 2015

(65) Prior Publication Data
US 2016/0331873 A1      Nov. 17, 2016

(30) Foreign Application Priority Data

Dec. 16, 2013   (EP) .................................. 13197577

(51) Int. Cl.
*D01D 5/00*      (2006.01)
*A61L 31/06*     (2006.01)
(Continued)

(52) U.S. Cl.
CPC ............. *A61L 31/06* (2013.01); *A61L 31/041* (2013.01); *A61L 31/148* (2013.01); *A61L 31/16* (2013.01);
(Continued)

(58) Field of Classification Search
CPC ........ A61L 31/06; A61L 31/16; A61L 31/148; A61L 31/041; A61L 2300/20;
(Continued)

(56) References Cited

U.S. PATENT DOCUMENTS 3,623,928 A * 11/1971  Wincklhofer et al. ..... C08J 9/24
                                                                                138/129
3,914,501 A * 10/1975  Miller .................... D04H 1/541
                                                                                156/155

(Continued)

FOREIGN PATENT DOCUMENTS

WO         WO 9917817 A1      4/1999

OTHER PUBLICATIONS

International Search Report received in PCT Patent Application No. PCT/EP2014/077754 dated Feb. 4, 2015 in 3 pages.

*Primary Examiner* — Paul B Prebilic
(74) *Attorney, Agent, or Firm* — Knobbe, Martens, Olson & Bear, LLP (57) ABSTRACT

The present invention relates to pore-free polymer tubes and prefers bio-resorbable pore-free polymer tubes prepared from at least one polymer filament, wherein the at least one polymer filament has a diameter of ≤50 μm and the at least one polymer filament is melted pore-free, as well as the methods to prepare these polymer tubes, which are especially useful for the production of stents.

7 Claims, 2 Drawing Sheets

(51) Int. Cl.
    *A61L 31/04*     (2006.01)
    *A61L 31/16*     (2006.01)
    *D01D 10/02*     (2006.01)
    *D01F 1/10*     (2006.01)
    *A61L 31/14*     (2006.01)
    *C08G 63/08*     (2006.01)
    *C08L 75/04*     (2006.01)

(52) U.S. Cl.
    CPC ........... *C08G 63/08* (2013.01); *D01D 5/0038* (2013.01); *D01D 10/02* (2013.01); *D01F 1/10* (2013.01); *A61L 2300/416* (2013.01); *C08G 2230/00* (2013.01); *C08L 75/04* (2013.01)

(58) Field of Classification Search
    CPC .... D01D 5/0038; D01D 5/0023; C08L 75/04; C08L 2203/00; C08L 2203/02
    See application file for complete search history.

(56) References Cited

U.S. PATENT DOCUMENTS

| | | | | |
|---|---|---|---|---|
| 3,978,192 A * | 8/1976 | Sussman | ................ | D01D 5/16 264/210.7 |
| 4,001,367 A * | 1/1977 | Guthrie | ................ | D01D 5/247 106/18.14 |
| 4,056,344 A * | 11/1977 | Lemelson | ............... | B29C 57/08 425/132 |
| 4,830,062 A * | 5/1989 | Yamamoto | ......... | B01D 39/1692 138/177 |
| 5,279,955 A * | 1/1994 | Pegg | ...................... | C12N 11/06 435/181 |
| 2001/0000189 A1* | 4/2001 | Hayes | ..................... | A61L 31/06 623/23.75 |
| 2003/0121594 A1* | 7/2003 | Brill | ...................... | B29C 53/74 156/162 |
| 2004/0037813 A1* | 2/2004 | Simpson | ................... | A61F 2/08 424/93.7 |
| 2005/0137675 A1* | 6/2005 | Dubson | ..................... | A61F 2/06 623/1.4 |
| 2010/0055154 A1* | 3/2010 | Liao | ...................... | A61K 9/0092 424/443 |
| 2010/0070020 A1* | 3/2010 | Hashi | ..................... | A61L 31/06 623/1.15 |
| 2010/0303881 A1* | 12/2010 | Hoke | ........................ | A61K 9/70 424/423 |
| 2011/0035023 A1* | 2/2011 | Maquet | .................. | A61L 27/20 623/23.65 |
| 2011/0062638 A1* | 3/2011 | Glauser | ................... | B29C 49/08 264/532 |
| 2013/0103139 A1* | 4/2013 | Hoffmann | ............... | A61L 31/10 623/1.46 |
| 2013/0264731 A1* | 10/2013 | Baier | ..................... | D01D 5/0076 264/10 |

* cited by examiner

PRODUCTION OF RESORBABLE POLYMER TUBES MADE OF THREADS

The present invention relates to pore-free polymer tubes, preferred from bio-resorbable polymers, made of at least one polymer filament, wherein the polymer filament has a diameter of ≤50 μm and the wound at least one polymer filament is melted pore-free, further a method to produce these polymer tubes, which are especially suitable for the production of stents.

The implantation of stent grafts such as stents is a common interventional procedure for the treatment of stenosis today. Usually, stents are prepared from metal alloys such as stainless steel, cobalt-chromium alloys, or nickel-titanium (e.g. nitinol). Such metal stents are known in large number and work well in practice. On the one hand, based on their metal structure and radial strength, such metal stents shall ensure that the blood vessels remain open after widening and stent implantation and that the blood flow is permanently maintained. On the other hand, stents serve in tumor therapy to prevent malignant tumor-induced constriction of respiratory tracts (windpipe), billary tracts, or esophagus or to keep them open after widening.

Stents are currently divided into two subtypes: permanent (bio-stable) and resorbable (degradable) stents. Permanent stent are furnished in such a way that they can remain in the blood vessel for an indefinite period of time. Resorbable stents, however, are degraded within the blood vessel over a defined period of time.

More recent investigations have shown that vascular stenoses do not require permanent support by endoprostheses especially in the form of stents. It is perfectly sufficient to support the blood vessel over a limited period of time until the traumatized tissue of the vessel is healed and the vascular smooth muscle cells have been regenerated. These cells assume again the responsibility to keep the blood vessel open and therefore the stent is no longer required and need not to remain in the vascular lumen. This temporary function of the vascular support is fulfilled by so-called resorbable stents that are degraded within the body.

Resorbable stents have the advantage that foreign material does not remain in the blood vessel permanently and thus the danger of an adverse vascular reaction such as Restenosis is limited in time. In children, an additional advantage of resorbable stents is that the blood vessels are not limited in their growths by a permanent vascular support.

Today, two different materials are used for bio-resorbable stents or are in clinical trials:
 Biopolymers, i.e. resorbable biopolymers, in particular polylactide
 Metals, in particular magnesium alloys Regarding the bio-resorbable metal stents, only the company Biotronik has commenced clinical trials with a bio-resorbable magnesium alloy. However, the company Lifetech (China) has performed animal trials with an iron-based, resorbable stent. No clinical or preclinical trials on animal models are known from other companies. Although the primary goal of absorption of the implanted stent is achieved for magnesium alloys, the problem so far is that the period of time degradation is not defined. Depending on the alloy, the material degradation is subject to fluctuations, difficult to control and generally too fast to ensure a save incorporation of the stent in the vascular walls and assume a supporting function until regeneration of the vessel section is completed. Due to uncontrolled degradation, pieces of the stent can detach and cause thrombosis.

Most developments of resorbable stents focus on biopolymers and herein on polylactides, also called polylactic acids (short PLA). They are technical biopolymers, belong to the polyesters, and are built up from many, chemically linked lactic acid molecules.

Of the polylactides, especially the poly-L-lactide (PLLA) and the polylactide-co-glycolide (PLGA) are used for resorbable stents.

First to receive CE-approval for the uncoated PLLA stent Igaki-Tamai® was Kyoto Medical in November 2007. Later, Abbott accomplished CE-approval for Absorb®, a PLLA stent with everolimus as active substance in a poly-D,L-lactide (PDLLA) coating. In 2013, Elixir received approval for its PLLA-based stent Desolve® with a Novolimus-containing coating.

Polylactides are readily available. There are several manufacturers with many years of experience. The material is considered biocompatible. In surgery, the bio-resorbable polylactide suture material is known and has been applied for years. Consequently, there are no objections to use polylactide as implant material and no extensive biocompatibility studies have to be performed. The resorbability can be precisely adjusted by choice of the suitable polylactide or material composition (copolymers). Currently, a total degradation i.e. the complete degradation of the stent or the stent struts within 18 months (1.5 years) post implantation is desired. The polylactides PLLA and PLGA exhibit as materials for stents, i.e. in the form of a pipe, in general a high elongation at break. Elongations at break up to 100% of a customary PLLA pipe (ø1.8×0.15 mm) are easily attainable, however with the disadvantage that the strength of these tubes is only 50-60 MPa (see FIG. 1). Strength-increasing measures lead, however, to a reduction of the elongation at break. Thus, there are several disadvantages in opposition to the advantages of the use of polylactides.

The namely greatest disadvantage of polylactides is the limited strength of the materials which is why strength-increasing processes are employed. PLLA tubes show a strength below 60 MPa (typically 50 MPa) in tensile tests. Because of this low strength of polylactides, high wall thickness is required for stent blanks (polymer tubes) and stent struts, respectively, to ensure that the stents have sufficient radial strength for vascular support.

Great efforts are made to increase the strength of the polymers or the tubes. Still, nowadays the pipe or wall thicknesses are at least 150 μM to ensure sufficient radial strength. With these wall thicknesses, small vascular diameters are not to be reached. These massive struts are in conflict with the trend to produce non-resorbable stents with ever thinner struts with strut profiles of merely 60 μm or below. Better healing chances of the blood vessel are expected from these delicate stents.

The strength-increasing measures lead in turn to a reduced elongation at break of the polymers which is why already small distension of the polylactide stents can lead to fractures of single struts. Despite the high strut profiles, the strength of the stent struts or bars is limited leading, in combination with the low elongation at break, to a costly and protracted procedure during stent implantation.

It is not recommended to implant PLLA stents directly ("direct stenting") but to widen the stenosized blood vessel with the help of balloon dilation first ("pre-dilation"). Partly, an atherectomy is further conducted i.e. hard deposits in the arteries are removed by means of minimal invasive methods. Afterwards, the vessel diameter should be measured precisely preferably using the IVUS or the OCT method to select the appropriate stent size and thus prevent an over- or under-expansion of the polylactide stent. Finally, the polylactide stent is inserted into the already opened and prepared blood vessel. A post-dilatation of the implanted stents with a non-compliant balloon catheter is additionally recommended.

An additional disadvantage of polylactide stents may here be the limited shelf life due to the sensitivity of the material against temperature and humidity. Unwanted degradation processes can commence early before implantation.

In general, polymers tend to creep and especially stretched polymer structures exhibit this behavior. Crimped stents on balloon catheters stretch very slowly causing the stent to lose firm fit on the balloon catheter. In the blood vessel widened stents contract again easily and thus decrease the blood vessel diameter, respectively the blood stream.

Tubes for the production of vascular implants or stents exhibit small diameters of typical below 3.0 mm. If these tubes consist of biopolymers, they are preferably prepared by extrusion. During production by extrusion, high-purity dry polylactide granules are melted in small extruders to a viscous substance and pressed continuously under high pressure by a worm drive through a nozzle in form of a pipe.

Another production method is injection moulding. For this purpose, by using an injection moulding machine the corresponding material is plasticized in the injection unit and injected into an injection mould. The cavity of the mould determines the form and surface structure of the finished part. Alternatively, polymer tubes can also be drawn from hollow bodies: tube drawing process.

It is common to the production processes of both extrusion and injection moulding that the long-chained polylactide molecular chains are largely undirected or slightly pre-oriented in pressing direction (axial pipe direction) and that the tubes are present in a largely tension-free state. The tensile strength of the tubes is low with 50 to 60 MPa. Sufficient radial strength of the stents can only achieved with these polylactide tubes by high wall thickness or large cross sections of the stent struts. There is the advantage of the polymer tubes prepared by extrusion or injection moulding and the stents derived therefrom that the polymer tubes and stents are not porous i.e. the polymer tubes and stent struts do not exhibit pores or gaps as is the case for polymer tubes from wound filaments and have thus the advantage to degrade uniformly under physiological conditions.

Here, polymer tubes, which are obtained by winding of polymer filaments using solution spinning or melting spinning, have the disadvantage that tissue-like or felt-like structures arise with pores or gaps between the wound filaments, such that no uniform biological degradation under physiological conditions can occur and such that fragments of such tubes can cause vascular complications up to cardiac infarction. However, the advantage of these polymer tubes made of wound filaments is the orientation of the molecular chains along the filament's longitudinal axis whereby a higher tensile strength is obtained so that such polymer tubes are only suitable for large body orifices and consist of non-bio-resorbable polymers like for example oesophagus stents in form of a tube of wound filaments with pores, which have a size preventing tumor cells to pass. Such an oesophagus stent is for instance disclosed in US patent application US 2013/103139 A1.

The laid-open publication of the US application US 2004/0037813 A1 discloses on a substrate electrodeposited collagen for the production of tissues and organs. FIG. 3 of US 2004/0037813 A1 shows a device for the application of the collagen on a rotating substrate and FIG. 10 shows a magnification of an electro-spun matrix made from collagen type I and type II in a 50:50 mixture. FIG. 12 shows a magnification of a felt from collagen type II and the FIGS. 14 and 15 show a stent before and after coating with collagen nanofilaments. The FIGS. 10, 12 and 15 of US 2004/0037813 A1 display a felt-like structure from disordered collagen filaments. Neither a directed winding of the collagen filaments nor a pore-free melting of the applied collagen filaments is disclosed in US 2004/0037813 A1. According to the disclosed procedures in US 2004/0037813 A1, there can be no pore-free melting of the collagen fibers.

The laid-open publication of the international application WO 99/17817 A1 discloses a porous tissue of disordered filaments as well as a device and a method for the productions of these tissues. FIG. 1 of WO 99/17817 A1 shows the device and FIG. 2 the tissue made from a maze of disordered filaments. Neither a pore-free polymer tube nor a directed or ordered orientation of the polymer filaments are disclosed in WO 99/17817 A1. WO 99/17817 A1 does also not describe the pore-free melting of the polymer filaments but rather a non-pore-free melting of the polymer filaments below the melting temperature.

The laid-open publication of the US application US 2010/0070020 A1 discloses an electro-spun base unit made of polyurethane filaments that is sheathed by a supporting tissue and again surrounded by an outer layer. FIG. 2A of US 2010/0070020 A1 shows an electron micrograph of arbitrary oriented polymer filaments. Neither a pore-free polymer tube nor an ordered orientation of the polymer filaments are disclosed in US 2010/0070020 A1.

The prior art does not disclose a polymer tube made from directionally wound polymer filaments, which are pore-free melted afterwards, such that a massive pore-free polymer tube results like in an extrusion or injection mould process, however with the inventive difference of the maintenance of the orientation of the polymer chains or molecular chain in the polymer filaments whereby an increased tensile strength is obtained and a restoring force in direction of the nominal diameter of the polymer tube is achieved.

In case of the polymer tubes prepared by extrusion or injection moulding, reinforcing measures have to be taken because the orientation of the molecular chains is missing. Furthermore, it is known that due to the shear forces in an extrusion process the average molecular weight of the employed polymer is reduced because of the cleavage of molecular chains. During solution spinning, the molecular weight of the polymers is maintained. In the competing processes of extrusion and injection moulding, the molecular weight is reduced by about 30-50%. This is primarily due to the high shear forces in the extruder worm and secondarily due to the high thermal stress that is exercised on the polymer during plasticizing. The molecular weight can be measured using viscosimetry by determining the inherent viscosity (IV). For this purpose, the transit time of a solubilized polymer is compared with the transit time of the pure solvent. A typical starting material like PL38 from Corbion Purac has an IV of 3.8 dL/g. In the extruder, the IV is reduced to 2.5 dL/g. In the following laser cutting (about 5% IV reduction) and sterilization (about 25% IV reduction), the polymer continues to lose molecular weight. In the inventive process, the molecular weight is only scarcely reduced during production of the polymer tubes (below 5%). The higher molecular weight is beneficial for the mechanical properties and also increase the absorption time because longer chains have to be cleaved more often.

It is known about thermoplastic synthetics that the material strengths can be increased by drawing. This procedure is frequently applied standardly in the industrial production of synthetic products.

During drawing, the long polymer molecules slide on each other, are disentangled and aligned in tensile direction. They become increasingly parallel in respect to each other. The orientation of the molecular chains is synonymous with a partial crystallization (semi-crystallization), whereas within the material tensions are induced at the same time (inner tension). The semi-crystalline order should be stabilized by secondary bonds (Van der Waals forces, dipole-dipole interaction, or hydrogen bonds) to prevent the loss of tension i.e. the tendency to creep towards the original shape. The drawing does not have to take place at room temperature necessarily. For example, the drawing of PLLA tubes can take place at temperature of typical 50° C. to 100° C.

This means that during drawing two processes occur in parallel: the molecules are aligned in tensile direction and the arising crystalline sections are rectified.

Figure 2:
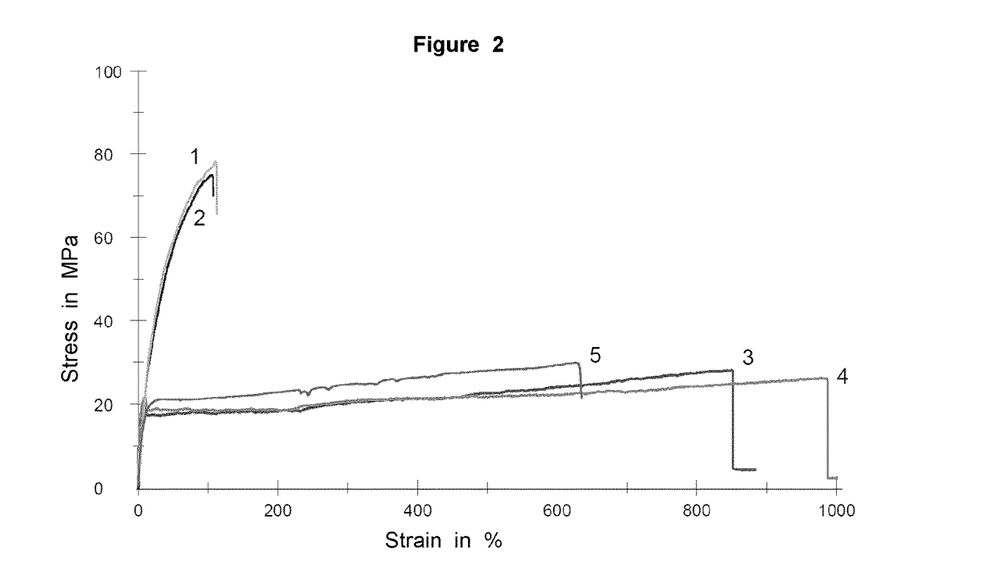
FIG. 2 shows the comparison between stress-strain diagrams of tubes prepared from PCL.

For drawing, the polymer tubes can be widened over a mandrel in order to prevent an increase in strength. Another method comes from balloon catheter production. Using the same installations and devices for dilated (moulding) of a balloon for a balloon catheter, a PLLA tube is expanded radially to a higher diameter. A similar process is disclosed in US2011/0062638 A1. FIG. 2 shows a stress-strain diagram of a radial expanded i.e. solidified PLLA tube using this procedure from the prior art. A substantially increased strength but also a reduced elongation at break can be seen. The reduced elongation at break leads to a limited extensibility of the polylactide stents and to a risk of breakage at only minimal over-extension over the nominal diameter of the stent. The nominal diameter of a stent refers to the inner diameter of the stent in the dilated, implanted state.

As has been pointed out, polymers such as polylactides as stent materials exhibit the decisive disadvantage of a limited strength which is why processes to increase strength are used. However, current strength-increasing methods such as the drawing lead to a limited extensibility and thereby to a severe constraint of the application of biopolymer stents.

The aim of the present invention is therefore to improve the strength of polymer tubes and stents made thereof or other vascular implants by suitable measures and processes and to provide polymer tubes as well as stents with improved elongation at break and restoring forces in direction of the nominal diameter. The inventive production of polymer tubes eliminates the severe constraints or improves the properties of the polymer tubes, which are thereby particularly suited for the production of stents.

The object of the invention is to provide a polymer tube that exhibits an increased radial strength at limited reduction of the elongation at break and is thus particularly suitable for the production of stents.

This objective is solved according to the invention by the technical teaching of the independent claims. Further advantageous embodiments of the invention result from the dependent claims, the description, the figures and the examples.

The present invention relates to a pore-free polymer tube and preferably to a bio-resorbable pore-free polymer tube prepared from at least one polymer filament, wherein the at least one polymer filament has a diameter of ≤50 μm and the at least one polymer filament is melted pore-free. The diameter of the inventively used polymer filament is ≤50 μm, more preferred ≤30 μm, more preferred ≤20 μm, more preferred ≤15 μm, further preferred ≤12 μm, further preferred ≤10 μm, more preferred ≤8 μm and even more preferred ≤5 μm and especially preferred ≤2.5 μm. The diameter of the polymer filament is preferred in the following ranges: between 50 nm and 50 μM, more preferred between 100 nm and 20 μM, more preferred between 150 nm and 10 nm, even more preferred between 200 nm and 5 μM and especially preferred between 300 nm and 2.5 μM. Another aspect of the present invention is a polymer tube prepared by the winding of at least one polymer filament, wherein the polymer filament has a diameter in the range from 50 nm to 50 μm.

As used herein, the term "pore-free" should be understood that the inventive polymer tube does not possess any pores like for example present in tissues or felts or web of disordered or arbitrarily oriented filaments. The filaments lie disordered on top of each other and the gaps in between the polymer filaments are referred to as pores. Even the melting of these felt-like or tissue-like or web-like structures cannot completely remove the pores, except the polymer filaments in these structures are completely liquefied, which would however destroy the felt-like or tissue-like or web-like structures and would thus be absurd. Thus, the term "pore-free" refers to a structure of the polymer tube according to the invention, which does not possess pores, wherein a pore is a gap with a volume of at least 900 nm$^3$ or a maximal diameter of at least 800 nm. The maximal diameter refers to the greatest possible diameter in a pore with any geometrical form. Pores refer to the inner volume of the tube and not to possible uneven material surfaces i.e. the inner as well as the outer surface of the polymer tube.

The term "pore-free" is furthermore defined as follows: A conventional extruded tube of the same material is measured in outer diameter and wall thickness. The volume is determined by the average outer diameter, the average wall thickness, and the measured length of the tube. Further, the mass of the tube is determined on a precision scale. The mass of the tube is divided by the volume. Thus, the average density of the tube is determined. Provided that the average density of the extruded polymer tube is maximal 5%, preferred not more than 3% of the average density of the tube prepared according to the invention, the inventive tube is referred to as "pore-free". Therefore, a polymer tube is "pore-free" if its average density is not greater than 5%, preferred not greater than 3% of the average density of polymer tube of the same material prepared by extrusion.

Thus, the present invention relates to a pore-free polymer tube and preferably a bio-resorbable pore-free polymer tube prepared by winding of at least one polymer filament, wherein the at least one polymer filament has a diameter of ≤50 μm and the at least one polymer filament is melted or more specifically pore-free melted.

Thus, the inventive pore-free and preferable bio-resorbable polymer tube does not consist of a filament tangle and does not consist of a tissue and does not consist of a felt. Furthermore, the wound polymer filaments form the polymer tube. The polymer filaments are not wound around a substrate or a medicinal product such as a stent and above all a metal stent on which the wound polymer filaments should remain. The inventive usage of a mandrel or a coil for winding the polymer filaments only serves to confer the polymer tube a defined inner diameter namely already the nominal diameter and to ensure a directed winding wherein the finished polymer tube is of course removed from the mandrel or coil. Thus, the inventive polymer tubes comprise no support frame such as a stent around which the polymer tube is located. The inventive polymer tube as well as the preferable laser-cut structure thereof form the stent themselves.

Further, the present invention relates to a pore-free and preferable bio-resorbable polymer tube prepared by directed winding of at least one polymer filament, wherein the at least one polymer filament has a diameter of ≤50 µm and the directed wound at least one polymer filament is melted or more precisely pore-free melted.

As used herein, the term "directed" refers to an ordered winding of the polymer filament or polymer filaments. A directed or ordered winding of the polymer filament or polymer filaments may imply the winding according to a certain pattern or the existence of a certain order at least in sections or layers of the polymer tube. Preferred is a winding like a cable on a cable drum. A directed or ordered winding does not exclude that the polymer filaments cross each other or lie on top of each other, wherein in certain sections or layers or films of the polymer tube the wound polymer filaments should be parallel to each other. Not directed or not ordered is the application of a solution of polymer filaments using a spray device or electrospinning such as revealed in US 2010/0070020 A1, WO 99/17817 A1, US 2004/0037813 A1 or US 2013103139 A1 because this results in an arbitrary orientation of the polymer filaments. However, the molecular chains or synonymously referred to a polymer chains, are already aligned along the longitudinal axis of the polymer filament, this orientation can be exploited to generate beneficial properties if the polymer filaments are wound or assembled to a polymer tube in an order or directed orientation as well. The opposite of a directed or ordered orientation is therefore the arbitrary or disordered orientation.

As used herein, the term "winding" is particularly important. In order to wind the at least one polymer filament directionally, the polymer filament is pulled off the spin nozzle or the electrospin nozzle. Thus, the spin nozzle does not spray the polymer filament on the mandrel or coil, whereby a winding and all the more a directed winding becomes impossible, but continuously produces a polymer filament, which can be referred to as an endless polymer filament, that is wound. The polymer filament or endless polymer filament so to speak joins the spin nozzle with the mandrel or the coil. Therefore, on the mandrel or the coil, an endless polymer filament is wound. However, no multitude of filament pieces, entangled filaments, tangles of filaments, or a felt is applied on the mandrel or sprayed or unloaded, which cannot occur directionally.

Moreover, the present invention relates to a bio-resorbable pore-free polymer tube prepared by winding of at least one polymer filament, wherein the at least one polymer filament has a diameter of ≤50 µm and the wound at least one polymer filament is melted while keeping the orientation of the molecular chains along the longitudinal axis of the filament, or more precisely pore-free melted.

Alternatively, the present invention relates to a pore-free polymer tube and preferable a bio-resorbable pore-free polymer tube prepared by directed winding of at least one polymer filament, wherein the at least one polymer filament has a diameter of ≤50 µm and the wound at least one polymer filament is melted while keeping the orientation of the molecular chains along the longitudinal axis of the filament, or more precisely pore-free melted.

According to the present invention, the wound or directionally wound polymer filaments are melted such that the pores are removed and a pore-free polymer tube results, wherein the melting is preferred at or maximal at 15° C., more preferably at maximal 10° C. above the melting temperature of the polymer filaments and moreover preferably occurs such fast that the orientation of the molecular chains along the longitudinal axis of the filament is maintained. Thus, a pore-free massive polymer tube is obtained like after extrusion or injection moulding but with the great difference that the orientation of the molecular chains is maintained along the longitudinal axis of the polymer filament. However, such an orientation of the molecular chains or the polymer chains cannot be obtained by an extrusion process or an injection moulding process.

The inventive polymer tubes preferably have an inner diameter of 0.25-20 mm, more preferably 0.5-15 mm, even more preferably of 1-10 mm, and most preferably of 1.5-5 mm. For example, for stents of the coronary blood vessels, typically tubes with an inner diameter of 2.0 to 4.0 mm are used with wall thickness of 100 to 200 µm. Accordingly, the outer diameters of the polymer tubes are 2.2 to 4.4 mm.

The tube and the appropriate filament are prepared from polymer material and preferably from a resorbable polymer. The polymer tubes have a circular cross section. As used herein, the term "wall" or "tube wall" refers to the lateral or cylindrical surface of the polymer tube and thus to the part of the polymer tube obtained by winding of at least one polymer filament without possible additionally applied coatings. The inventive polymer tube has only one seamless wall. As used herein, the term "wall thickness" refers to the inner and outer dimensions, thus the outer and inner diameter of the tube.

As used herein the term "resorbable" or "bio-resorbable" means that the polymer or the polymer tube, or the stent prepared therefrom, degrade slowly in the human or animal organism over a defined time and that at some point only the degradation products exist in the body and are preferably excreted form the body. At this time point, the solid parts or fragments of the polymer are not present anymore. The degradation products should be physiologically essentially harmless.

According to the invention it is preferred that the polymer tube is prepared from at least one thermoplastic polymer and more preferred from a thermoplastic bio-resorbable polymer. Thermoplastic bio-resorbable polymers can be selected from the following group comprising or consisting of:

poly(ε-caprolactone), polyurethane, polyhydroxybutyrate, polylactonic acid, polyglycolic acid, polylactide, polyglycolide, copolymers of the polylactides and polyglycolides, polydioxanones, polyethylene glycols (PEG), polypropylene carbonate (PPC), poly(desamino tyrosyl-tyrosine-ethyl ester carbonate) (PDTE carbonate).

Examples for non-bio-resorbable polymers are nylon, poly(methyl methacrylate) (PMMA), polyamide (PA), polycarbonate (PC), polyethylene terephthalate (PET), polypropylene (PP), polystyrene (PS), poly ethylene (PE), silicones, polytetrafluoroethylene (PTFE), polyvinylchloride (PVC).

Since the application of solution spinning or electrospinning is preferred, the bio-resorbable polymers should be soluble in an organic solvent such as acetone, methanol, ethanol, THF, methylene chloride, benzene, toluene, chloroform, tetrafluoroethylene (TFE), carbon tetrachloride, ethyl acetate, diethyl ether, acetonitrile, 3-pentanone, butanone, propanol, hexafluoroisopropanol (HFIP). Excluded from the present invention because unsuitable is collagen. However, preferred is polylactide such as PLLA as well as copolymers from polylactide and polyglycolide such as PLGA.

Another aspect of the invention relates to pore-free polymer tubes prepared from at least one polymer filament, wherein the polymer filament has a diameter preferably in the range from 50 nm to 50 µm and the polymer filaments consist of different, preferred bio-resorbable polymers. Another aspect of the invention relates to the polymer tubes prepared from several polymer filaments, wherein the polymer filaments have a diameter preferably in the range between 50 nm and 50 μm and the polymer filaments consist of different preferably bio-resorbable polymers. The inventive preparation of the polymer tubes by winding of polymer filaments allows the combination of different polymers or copolymers in the polymer tubes (subsequently called hybrid tubes), wherein the different polymers or copolymers may exist in a targeted, for the final product beneficial, orientation. As a result, the inventive polymer tube can be conferred specifically properties of different polymers or copolymers. With the choice of different polymers, hybrid tubes are producible that are specifically matched to the use. According to the present invention, the use for the production of stents and other blood vessel prostheses is preferred. In this case, the polymer tubes can be matched exactly to the physiological properties of the human blood vessels or the healing processes and degradation processes.

For example, the tubes can consist of different polymers in layers. The inner (facing the lumen) and the outer (facing the vessel wall) layer of the wall of the inventive polymer tube can preferably consist of a polymer with very slow degradation whereas in between in the inside of the wall a polymer with high strength (but if necessary fast degradation) is used.

Next to the combination of different polymers in layers in the wall of the polymer tube (radial polymer combination) are also polymer tubes producible, according to the present invention, that exhibit along the length of the tube different polymers and thus different properties (axial polymer combination). This means that different polymers may vary or be arranged in both layers and rings in the wall of the polymer tube.

Any combinations of different polymers in radial and axial direction are possible. In one embodiment of the present invention, the polymer tubes are prepared from a polymer filaments and the polymer filament consists of different polymers. However, the invention also comprises polymer tubes prepared from at least two polymer filaments consisting of different polymers preferably resorbable polymers.

Moreover, it is preferred if the inventive polymer tubes have a wall thickness of ≤250 μm (for example for peripheral blood vessels), more preferably ≤200 μm, more preferably ≤150 μm (for example for coronary blood vessels), and most preferably ≤100 μm. Another aspect of the present invention relates to polymer tubes that are wound to different wall thicknesses along the length of the tube. These wall thicknesses should meet the strength required of the parts of the polymer tubes prepared according to the invention.

The inventive polymer tubes have at least 5, preferably at least 10 and even more preferably at least 20 layers of polymer filaments. One layer consists of the windings of at least one polymer filament that run in one plane that is parallel to the axis of the polymer tube i.e. the thickness of the layer corresponds to the diameter of the polymer filament.

In the pore-free polymer tubes prepared in accordance with the present invention, the polymers have preferably long molecular chains, which are aligned along the longitudinal axis of the filament, especially if the filaments are prepared by solution spinning. This is beneficial for the strength and the slower degradation of the polymer tubes. Due to the orientation of the molecular chains along the longitudinal axis of the filament, a restoring force is built up in case of deformation of the polymer tube or of a stent prepared from the polymer tube, which is directed to restore the tube or the stent to the outer diameter of the mandrel i.e. the nominal diameter. The outer diameter of the mandrel corresponds to the inner diameter of the polymer tube or the stent after melting of the aligned molecular chains. It is in accordance with the present invention that the polymer tube and therefore also the stent produced from the polymer tube preferably by laser cutting are produced in the nominal diameter i.e. the outer diameter of the mandrel corresponds to the inner diameter of the polymer tube after dilatation, such that in the crimped polymer tube or the crimped stent a restoring force in direction of the nominal diameter is built up. In the prior art, such polymer tubes are prepared by extrusion, wherein during extrusion no alignment of the molecular chains occurs causing extruded tubes to have lower tensile strengths and elongations at break compared to the inventive tubes and that because of the disordered and arbitrary orientation of the molecular chains no or a substantially smaller restoring force in direction of the nominal diameter is built up.

A preferred embodiment of the invention relates to a polymer tube comprising at least on active agent. It is preferred that the at least active agent is inside the wall of the polymer tube. The preferred active agents are suitable for the reduction of a restenosis. Suitable active agents are namely anti-proliferative or anti-restenotic active agent.

The at least one used anti-proliferative or anti-restenotic active agent is preferred selected from the group comprising or consisting of: paclitaxel, rapamycin, and their derivatives such as 6-α-hydroxy-paclitaxel, baccatin or other taxoteres, biolimus A9, myolimus, novolimus, pimecrolimus, tacrolimus, temsirolimus, zotarolimus, everolimus, ridaforolimus or other so-called "limus" derivatives (also called rapalogs).

Other combinations of active agents may be used. The concentration of the active agents may vary at different sections of the inventive polymer tubes such that, for example, the ends of the tube may contain more active agents than the center section. The concentration of the active agent may also vary in course of the wall thickness and for example exhibit a gradient such that on the outer surface (abluminal surface) of the polymer tube more active agent is present than in the inside of the tube (luminal surface) or vice versa.

For an improved radiopacity of the implanted stents in the body, either materials with higher density i.e. higher radiopacity are used for the preparation of the stents (e.g. the material PtCr in the Boston Scientific "Element" stent) or preferably so-called radiographic markers are inserted in the proximal and distal ends of the stents. The radiographic markers consist of, for example, tantalum, platinum, or exceptionally gold, and are crimped in small marker eyelets and often additionally laser-welded.

There are several possibilities in the inventive polymer tubes to produce radiopacity. The radiographic markers can be incorporated i.e. integrated into the tube wall in form of small round pellets or discs (similar to contemporary radiographic markers) or thin foils or wires during winding of the tube.

However, the preferred method is to already include the radiographic marker such as a powder of radiopaque materials like wolfram, tantalum, platinum, gold in the filament during preparation of the thin polymer filament. During winding, the radiopaque materials are therefore incorporated over the entire tube wall strength or preferably only in certain layer and/or certain sections of the polymer tube. The powders have a particle size smaller than 10 μm, preferably smaller than 5 μm, and even more preferably small than 1 μm. The powders or radiographic markers are dissolved from the implanted polymer stents during degradation. Due to their particle size and their bio compatibility (microbial inertness), radiographic markers are safe for the human organism.

By incorporation of the radiopaque powder or radiographic markers, for example, inly in the inner core of the polymer tube wall it is ensured that radiopacity is maintained until almost complete degradation of the stent. In contrast, if the radiopaque powders are only incorporated in the outer surface layers of the tubes (not in the core of the tube wall), the degradation process i.e. the degradation of the stents cannot be determined, for example, based on the remaining radiopacity.

Another embodiment of the present invention is that the radiopaque powders or the radiographic markers are not incorporated along the entire tube length but are only incorporated annularly in certain distances. The distances of the radiopaque rings should mainly correspond to the length of the stent, which is laser-cut from the tubes. In this way, stents are obtained with radiopacity only at the proximal and distal ends of the stent.

Any other possible embodiment i.e. the incorporation of the radiopaque powder or of the radiographic markers in the polymer tube is conceivable and possible.

Instead or in addition of the listed active agents or radiographic markers, particles or nanoparticles with physical (e.g. magnetic or radioactive) and/or chemical (e.g. alteration of pH) and/or physiological (e.g. antibacterial) modes of action can be incorporated in the tube walls.

Incorporated radioactive particles can serve, for example, to prevent a strong proliferation during blood vessel healing. Chemical particles can contribute to buffer the pH value, for example in stents from polylactides because the resorbable material decomposes to acidic lactic acid degradation products.

Likewise, additional short filaments of another polymer or a metal material can be incorporated into the polymer tube to improve the strength. These strength-improving filaments can be bio-resorbable as well or bio-stable. Namely if the additional filaments consist of a non-bio-degradable material, the length of the filaments should be preferably less than 50 μm, more preferably less than 20 μm and most preferably 10 μm and less.

In principle, using the inventive preparation of the polymer tubes from filaments and the addition of additives, tubes of diverse modes of action and properties can be prepared.

Furthermore, the present invention relates to a method for the preparation of a pore-free polymer tube, preferably a (bio-)resorbable polymer tube, comprising at least the following steps:
  a) winding of at least one polymer filament with a diameter ≤50 μm
  b) pore-free melting of at least one wound polymer tube.

Herein, the diameter of the polymer tube is ≤50 μm and preferred ≤30 μm, and more preferred ≤20 μm, more preferred ≤15 μm, and even more preferred ≤10 μm and most preferred ≤2.5 μm. The polymer filaments used according to the present invention are preferred round fibers, which means that they have a round cross section, but can also have other cross section such as oval or angular. Also, polymer filaments with a hollow cross section, i.e. hollow fibers, are possible.

According to the present invention, it is preferred if the at least one polymer filament in step a) is wound on a rotating mandrel. The mandrel has preferably a constant diameter, but can also be conic or wavelike shaped such that the diameter of the polymer tube varies along the length of the tube while maintaining the wall strength. In the inventive polymer tubes, which are used for the preparation of stents, it is especially preferred, if at least the inner diameter is constant along the entire length of the polymer.

The at least one polymer filament is wound directionally according to the present invention. Thereby, in certain sections of the polymer tube or in certain layers or over the entire polymer tube, the polymer filaments obtain a defined orientation, wherein thus in turn the molecular chains of the different polymer filaments, which are aligned along the longitudinal axis of the respective polymer filament, receive a defined orientation in respect to each other, such as conical layers around the longitudinal axis of the polymer tube. Due to this directed winding of the polymer filaments, the polymer tube is awarded beneficial properties such as an increased tensile strength or an increased dimensional stability in the nominal diameter as well as a restoring force of a deformed polymer tube or of a deformed stent produced therefrom, wherein this restoring force returns the deformed polymer tube as well as the deformed stent to the nominal diameter, be it from an overstretched or compressed shape. Therefore, it is also important that the polymer tube already possesses the nominal diameter during preparation i.e. the polymer filaments are wound on a mandrel or a coil, which has an outer diameter corresponding to the inner diameter of the polymer tube or the stent produced therefrom, which the polymer tube or the stent should have after dilatation in the blood vessel.

The filament is preferably deposited on a rotating mandrel with a deposition velocity of at least 100 m/min, more preferably of at least 300 m/min and even more preferably of at least 600 m/min. These high deposition velocities are on the one hand beneficial due to the high speed of the filament production and on the other hand desired to limit the winding times for one tube in case of very thin filaments.

For the preferred deposition velocities of the filament, corresponding preferred rotational velocities of the mandrel of at least 10,000 rpm, more preferred 30,000 rpm, and even more preferred 50,000 rpm and especially preferred 65,000 rpm.

For the preparation of a pore-free polymer tube and preferably a bio-resorbable pore-free polymer tube, a preferred method results that comprises the following steps:
  a) winding or directed winding of at least one polymer filament with a diameter of ≤50 μm on a rotating mandrel to a polymer tube; and
  b) pore-free melting of the at least one wound polymer filament.

Moreover, it is preferred if the polymer filament, which is wound to a polymer tube according to the present invention, is prepared by solution spinning or melting spinning. In solution spinning, the polymer is liquefied by a solvent, in melting spinning by heating. Especially preferred are the inventive methods, wherein the at least one polymer filament is prepared by solution spinning or melting spinning while at the same time it is wound on a mandrel. Also, it is preferred if the used polymer filament is an endlessly running filament or strand. This endlessly running polymer filament is cut after reaching the desired wall thickness.

One especially preferred form of solution spinning is electrospinning. In electrospinning, very thin fibers or filaments of polymer solutions are produced by treatment in an electric field. Here, the polymer solution is dosed at one electrode and removed by the electric field and accelerated. The solvent evaporates in case of this extremely thin filament very quickly and an order of polymer chains to crystallites arises (polymer crystallization from solution).

On the rotating mandrel, the preferably endlessly running polymer filament, preferably prepared from resorbable polymers, is wound evenly by a device until a pre-determined wall thickness is reached. A tube wound from one polymer filament is obtained, wherein the filament or filaments are ideally perfectly parallel in respect to each other. Herein, it is especially preferred if the at least one polymer filament is wound such that a lateral surface or polymer tube wall emerges, which is without gaps or continuous. The inventive polymer tube has thus preferably no disruptions.

The pores between the filaments are closed by subsequent melting of the filaments. The melting of the filaments can occur such that the alignment of the filaments is not lost. It is especially preferred if the melting of the at least on polymer filament occurs under vacuum. This can take place in a vacuum chamber, for example. Due to the generation of the vacuum, the air is eliminated from the still exiting minimal gaps of the closely juxtaposed filaments and the thus generated polymer tubes produced by melting are particularly pore-free like polymer tubes produced by extrusion or injection moulding. The melting of the wound polymer filaments and preferably of the directionally wound polymer filaments occurs preferably in the melting range of the employed polymer or in a range up to maximal 15° C., preferably up to maximal 10° C., more preferably up to maximal 5° C. above the melting point or the melting range of the employed polymer and preferably also only for a short time like for example 5 seconds to 180 seconds, preferred 20 seconds to 120 seconds, such that the alignment of the molecular chains is maintained. The molecular chains or synonymously called polymer chains are aligned along the longitudinal axis of the polymer filament.

Thus, the present invention relates to an additional preferred method for the preparation of a pore-free polymer tube and preferred a bio-resorbable pore-free polymer tube comprising the following steps:
a) winding or directed winding of at least one polymer filament with a diameter of ≤50 µm preferably on a rotating mandrel;
b) pore-free melting of at least one wound polymer filament, wherein the wound at least one polymer filament is melted pore-free while maintaining the alignment of the molecular chains along the longitudinal axis of the filament.

Another aspect of the present invention relates to a method for the preparation of a pore-free polymer tube and preferred a bio-resorbable pore-free polymer tube comprising the following steps:
a) winding or directed winding of at least one polymer filament with a diameter of ≤50 µm preferably on a rotating mandrel to a polymer tube;
b) pore-free melting of at least one wound polymer filament under vacuum.

Another aspect of the present invention relates to a method for the preparation of a pore-free polymer tube and preferred a bio-resorbable pore-free polymer tube comprising the following steps:
a) winding or directed winding of at least one polymer filament with a diameter of ≤50 µm preferably on a rotating mandrel to a polymer tube;
b) pore-free melting of at least one wound polymer filament under vacuum at a temperature within the melting range or up to 15° C. above the melting range of the polymer or the wound polymer filament.

Thus, the polymer tubes prepared according to the invention are already present in crystalline or semicrystalline form, without need of drawing. The crystallinity is generated by both the alignment of the molecules in the polymer filaments as well as the directed winding of the polymer filament/the polymer filaments. A preferred embodiment thus comprises a polymer tube prepared from at least one wound polymer filament, wherein the polymer filament has a diameter in the range of 50 nm to 50 µm and the single windings of the polymer filament, at least in the pre-defined sections, are parallel with respect to each other. These sections may be, for example, single layers of windings but also sections of the polymer tube from which a strut of a stent will emerge later and in which the direction of the filament or the angle of the winding corresponds to the future stress of the strut.

As used herein, the term "winding" refers to the winding of at least one polymer filament around an axis. Multilayer windings consist of concentric spiral coils that lie above each other. All windings of the least one polymer filament that run parallel to the axis of the polymer tube in one plane form a layer in the wall of the polymer tube.

The thermal melting of the wound polymer filaments can be conducted according to the invention as follows:

The wound polymer filaments from step a) can be melted still on the mandrel under increased temperature and additional pressure from the outside to close the pores. For example, the pressure can be generated by an adjacently attached roller on the outside.

Another method is the expansion of the in step a) wound polymer tube under temperature and pressure from the inside, wherein aside from melting the filaments are stretched at the same time. This procedure is similar to the balloon production (the balloon blowing) in the balloon catheter production.

Surprisingly, it could be shown that the elongations at break of a polymer tube prepared according to the present invention show a high directionality (see FIG. 2). It is suspected that this can be delineated to the unidirectional aligned polymer molecules. Moreover, it is especially beneficial that the elongation at break along the direction of the molecular chains despite the high tensile strength is very high with over 100% in the inventive polymer tubes, i.e. the tenseness (inner tension) of the material is very low. This is a fundamental, decisive advantage compared to the tubes rigidified by drawing from the prior art, wherein the elongation at break is reduced for high tensile strengths.

Nonetheless, the increased strength of the polymer tubes prepared according to the present invention may be further increased by drawing, i.e. stretching or rigidifying of the polymer tube. Preferred are herein the following procedures:
Already during winding on the mandrel, the polymer filaments (with the already aligned molecule chains) can be elongated.
A rigidifying can take place by expanding of the wound but not yet melted tube.
An additional combination of both procedures (elongation of the filament during winding and additional subsequent drawing of the tube) is possible.
It is possible to combine the melting of the filaments with the drawing of the wound tube in one thermo-mechanic process.
The finished tube (wound and melted) can be drawn by a subsequent expansion.

A preferred inventive method for the preparation of a polymer tube thus comprises that the at least one polymer filament in step a) is elongated during winding on the rotating mandrel and thus rigidified.

Another preferred inventive method for the preparation of a polymer tube is the result of the expansion to a nominal diameter and thus rigidifying of the polymer tube before step b), during the melting according to step b) or after step b).

Therefore, the following, for the purpose of the invention preferred methods for the preparation of a polymer tube result:

Method for the preparation of a pore-free polymer tube and preferred a bio-resorbable polymer tube comprising the following steps:
a) winding or directed winding of at least one polymer filament with a diameter of ≤50 µm preferably on a rotating mandrel to a polymer tube; and drawing of at least one polymer filament during winding;
b) pore-free melting of at least one wound polymer filament.

For drawing, the filaments, for example, are put under tension for deformation such that the disordered polymers and the semicrystalline sections are aligned parallel in respect to the tensile direction.

Method for the preparation of a pore-free polymer tube and preferred a bio-resorbable polymer tube comprising the following steps:
a) winding or directed winding of at least one polymer filament with a diameter of ≤50 µm to a polymer tube;
a') Rigidifying by expansion of the polymer tube;
b) Melting of the at least one wound polymer filament.

Method for the preparation of a pore-free polymer tube and preferred a bio-resorbable polymer tube comprising the following steps:
a) winding or directed winding of at least one polymer filament with a diameter of ≤50 µm to a polymer tube; and drawing of at least one polymer filament during winding;
a') Rigidifying by expansion of the polymer tube;
b) Pore-free melting of the at least one wound polymer filament.

Method for the preparation of a pore-free polymer tube and preferred a bio-resorbable polymer tube comprising the following steps:
a) winding or directed winding of at least one polymer filament with a diameter of ≤50 µm to a polymer tube;
b) pore-free melting of at least one wound polymer filament and drawing of the polymer tube parallel to melting.

Method for the preparation of a pore-free polymer tube and preferred a bio-resorbable polymer tube comprising the following steps:
a) winding or directed winding of at least one polymer filament with a diameter of ≤50 µm to a polymer tube;
b) pore-free melting of the at least one wound polymer filament;
b') drawing of the melted polymer tube by stretching.

The drawing of the polymer tube prepared according to the invention may occur at room temperature but preferably at elevated temperature.

To adjust and/or fixating the mechanical properties of the inventive polymer tubes, especially if drawing occurred, a thermal follow-up treatment can be conducted. By tempering at temperatures below the melting point, the crystallinity is increased. By quenching, these crystalline structures, but also the amorphous structures can be fixated.

Surprisingly, it was found that polymer tubes prepared by winding of as thin as possible polymer filaments, for example, on rotating mandrels, exhibit an increased strength with optimal elongation at break at the same time. Within the thin filaments with diameters in the micrometer or sub-micrometer range (with a diameter in the range of 50 nm to 50 µm), the molecules are already largely unidirectionally aligned.

As explained, the current strength-increasing methods, applied to state-of-the-art polymer tubes, lead to significant restrictions in the use as starting material for polymer stents. The inventive preparation of polymer stents eliminates these significant restrictions or improves the properties of the tubes, which is particularly decisive for their use for the preparations of stents and other blood vessel implants.

During drawing (stretching) of polymer tubes, two effects occur, in principle, in parallel.
A) The single long-chained molecule are disentangled and stretched along the stretching direction. In direction of the molecule chains, the strength is increased and orthogonal to the molecular direction decreased.
B) During stretching, the molecular chains are also moved in respect to each other, glide on top of each other, and are tensed in respect to each other (rigidified). Inner tensions arise. With increasing inner tensions, the elasticity of the material decreases.

Thus, the drawing is only possible to a limited extend because the polymer tubes can only be stretched to a limited extend without induction of break. On the one hand, molecules cannot be stretched to any extend and, on the other hand, the inner tensions are not allowed to overcome the breaking strength.

According to the invention, the processes of molecular alignment and rigidifying during the inventive preparation of the polymer tubes should be completely, at least largely, separated from each other to achieve an optimum for both processes.

The molecular alignment is already provided in the first step of the preparation of the polymer tubes, namely the winding of the polymer filaments. The tube preparation takes place by winding of as thin as possible polymer filaments, preferred on fast-rotating mandrels, shafts, or coils. Within the thin filaments with diameters in the micrometer range (≤50 µm) or sub-micrometer range (≤1 µm), the molecules are already largely unidirectionally aligned. The filament production may, for example, take place by extrusion from smallest spin nozzles (melting spinning) or preferably by solution spinning and more preferred by electrospinning. A stretching or rigidifying takes place afterwards in one or several additional steps.

Another preferred embodiment of the present invention relates to so-called hybrid-polymer tube as well as the stents produced thereof.

A hybrid-polymer tube consists of at least two polymers with different melting points. The melting points of the two enclosed polymers are at least 10° C. more preferred at least 20° C. apart from each other. The shaping of the tube structure is carried out such has been disclosed before, however, the introduction of the polymers takes place alternately, wherein the polymer with the highest melting point should not be wound at first and not at last. One layer consists of at least one filament layer. The melting of the filaments is conducted above the melting point of the polymer with the lower melting point but below the melting point of the polymer with the higher melting point.

By generation of different layers of filaments and pore-free melted polymer layers, the high tensile strength of filaments is combined with the advantages of pore-free surfaces. Thus, implants that consist of these hybrid-polymer tubes can be implanted like conventional implants, however, they have higher strengths at the same time. Furthermore, the absorption behavior can be adjusted by the choice of the polymer layers. The pore-free layers keep the tube together and ensure for the load-bearing capacity orthogonal to the fiber orientation. By contrast, the load-bearing capacity along the fiber orientation is performed by the high-tenacity and non-melted polymer filaments.

Thus, the present invention also relates to hybrid-polymer tubes that are prepared by winding or layer-wise winding of at least one polymer filament of a polymer A, wherein the at least one polymer filament of the polymer A has a diameter of ≤50 μm, and winding of at least one polymer filament of a polymer B, wherein the at least one polymer filament of the polymer B has a diameter of ≤50 μm, on top of the layer of at least one polymer filament of polymer A and winding of at least one polymer filament of polymer A, wherein the at least one polymer filament of the polymer A has a diameter of ≤50 μm, on top of the layer of at least one polymer filament of polymer B, wherein the at least one polymer filament of polymer A within the layer of polymer A is melted at a temperature at or above the melting point of polymer A but at or below the melting point of polymer B, wherein polymer B has an at least 10° C. higher melting point compared to polymer A.

In other words, the present invention relates to a hybrid-polymer tube, prepared by winding or layer-wise winding of polymer filaments of a polymer A, wherein the polymer filaments of polymer A have a diameter of ≤50 μm, and winding of polymer filaments of a polymer B, wherein the polymer filaments of polymer B have a diameter of ≤50 μm, on top of the layer of polymer filaments of polymer A and winding of polymer filaments of polymer A, wherein the polymer filaments of polymer A have a diameter of ≤50 μm, on top of the layer of polymer filaments of polymer B, wherein the polymer filaments of polymer A within the layer of polymer filaments of polymer A are melted with each other at a temperature at or above the melting point of polymer A but at or below the melting point of polymer B, wherein polymer B has an at least by 10° C. elevated melting point compared to polymer A.

In yet other words, the present invention relates to a hybrid-polymer tube comprising several layers of wound and melted within the respective layer polymer filaments of a polymer A and in between the layers of wound and melted polymer filaments of polymer A layers of wound and not melted within the respective layer polymer filaments of a polymer B, wherein the polymer B has an at least 10° C. higher melting point compared to polymer A. The melting of the wound polymer filaments of polymer A within the respective layer occurs at a temperature above the melting point of the polymer A but below the melting point of polymer B.

According to the invention, the winding of the filaments of the polymer A as well as of the polymer B occurs directionally. As already disclosed, the winding of the polymer filaments occurs on a rotating mandrel or a rotating coil.

Accordingly, the present invention relates to a method to prepare a hybrid-polymer tube comprising the following steps:
 a) winding of at least one polymer filament of a polymer A with a diameter of ≤50 μm; and
 b) winding of at least one polymer filament of a polymer B with a diameter of ≤50 μm on top of a layer of the at least one polymer filament of polymer A; and
 c) winding of at least one polymer filament of polymer A with a diameter of ≤50 μm on top of the layer of the at least one polymer filament of polymer B; and
 d) optional multiple repetition of the steps b) and c); and
 e) melting or pore-free melting of the at least one wound polymer filament of polymer A within the respective layer of the at least one polymer filament of polymer A at a temperature at or above the melting point of polymer A but at or below the melting point of polymer B, wherein polymer B has an at least 10° C. higher melting point than polymer A.

Under these conditions, the at least one polymer filaments within the respective layer of at least one polymer filament of polymer B are not melted with each other.

Alternatively, the present invention relates to a method for the preparation of a hybrid-polymer tube comprising the following steps:
 a) winding of polymer filaments of a polymer A with a diameter of ≤50 μm; and
 b) winding of polymers filaments of a polymer B with a diameter of ≤50 μm on top of a layer of polymer filaments of polymer A; and
 c) winding of polymer filaments of polymer A with a diameter of ≤50 μm on top of the layer of polymer filaments of polymer B; and
 d) optional multiple repetition of the steps b) and c); and
 e) melting or pore-free melting of wound polymer filaments of polymer A within the respective layer of polymer filaments of polymer A at a temperature at or above the melting point of polymer A but at or below the melting point of polymer B, wherein polymer B has an at least by 10° C. elevated melting point than polymer A.

Further, the present invention relates to a method for the preparation of a hybrid-polymer tube comprising the following steps:
 a) alternated winding of layers of polymer filaments of a polymer A with a diameter of ≤50 μm and of layers of polymer filaments of a polymer B with a diameter of ≤50 μm, wherein the polymer with the lowest melting point forms both the undermost and uppermost layer; and
 b) Melting or pore-free melting of layers of the polymer filaments of polymer A at a temperature at or above the melting point of polymer A but at or below the melting point of polymer B, wherein polymer B has an at least by 10° C. elevated melting point than polymer A.

Stents cut from these hybrid-polymer tubes preferably by laser-cutting have special properties because they maintain the beneficial properties of polymer filaments in the layers of polymer B and, in addition, have very good stability and strength due to the melted layers of polymer A. The hybrid-polymer tubes as well as the stents prepared thereof can also be prepared from more than 2 polymers and can contain the active agents and/or radiographic markers as disclosed herein. Thus, the methods for the preparation of a hybrid-polymer tube can also comprise the step: Cutting a stent from a hybrid-polymer tube, preferably using laser. The diameter of the hybrid-polymer tube corresponds preferably to the nominal diameter of the stents. Accordingly, the methods for the production of a hybrid-polymer tube can alternatively comprise the step: cutting of a stent from a hybrid-polymer tube, preferably using laser, wherein the diameter of the polymer tube corresponds to the nominal diameter of the stents.

Another aspect of the present invention relates to the laser-cut stents from polymer tubes consisting of directionally wound polymer filaments that are not pore-free melted with each other. Due to the laser cut, the cut polymer filaments are melted along the cutting edge with each other such that no single filaments can detach from the ready-cut stent but due to the maintained filament structure, the stent exhibits beneficial properties concerning tensile strength and restoring force in direction of the nominal diameter.

The strong directionality of the strength of the tube prepared according to the invention can be used particularly for the preparation of blood vessel implants, preferably stents and especially preferred bio-resorbable stents. Herein, the term stents refers to lattice-like or web-like endoprostheses that are implanted into a hollow organ or body cavity to keep it open. The backbone of a stent, herein defined as the polymeric struts without coating, form no massive tube, but a braided mesh. For example, closer inspection of the backbone of a vascular stent reveals that it is cut from a massive tube e.g. using laser such that single, as thin as possible struts result, which are interconnected. The alignment and shaping of the struts and nodes is defined as stent design. For the purpose of the present invention, all common stent geometries can be used.

Stents or vascular supports need a high radial strength to keep the blood vessel open after dilatation (expansion). Conversely, in axial direction i.e. longitudinal direction of the stents, no high strength is required. Additionally, in radial direction (circumferential direction) a high elongation at break is required in order to expand the stent sufficiently and with risk of breakage during implantation using a balloon catheter. The polymer tubes prepared according to the invention have exactly these properties. They are distinguished by high strength and, at the same time, high elongation at break in radial direction i.e. circumferential direction.

A preferred aspect of the present invention is thus to provide polymer tubes that are particularly well suited for the production of stents. These polymer tubes, preferably resorbable polymer tubes, can be produced according to a herein described inventive method.

Moreover, the present invention thus comprises a stent or a vascular implant, preferred an resorbable stent, produced from one of the herein disclosed polymer tubes. This resorbable stent is preferred a stent for blood vessels, urinary tract, respiratory tract, bile ducts, or the digestive tract. Again, among these stents, stents for blood vessels or more general for the cardiac system are preferred.

During cutting of a stent, areas between the single struts are cut. A stent or a vascular implant has thus a variety of massive backbone components (e.g. struts in form of rings, spirals, waves, and wires) as well as numerous gaps between these massive components. In the common embodiment of endoprostheses or stents, the struts converge to nodes. However, there are also embodiments of endoprostheses in which no or almost no nodes are present and the struts have e.g. the form of rings or spirals. Preferred, these are balloon-expandable stents, which are pushed to the diseased position or to the position to be treated using a catheter, where the stents are dilated to their defined nominal diameter.

Further, a creeping of the material i.e. the crimped or in the blood vessel dilated stents is not desired which can be achieved by limiting the stretching or the drawing. To prevent undesired creeping processes of the implanted stents, it has been found advantageous, according to the invention, to produce the stents in the stretched state using laser cutting. This means that the stents are produced from the inventive polymer tubes, whose diameter corresponds to the nominal diameter which is to say the inner diameter of the stent in the dilated state. Afterwards, the inventive stent can still be applied (crimped) on a catheter balloon without difficulties. Thus, the invention relates to stents produced from the inventive polymer tubes, wherein the inner diameter of the polymer tube (the not dilated polymer tube) corresponds to the inner diameter of the stent after implantation.

Hence, the inventive polymer tubes for the production of a stent have preferably an inner diameter that corresponds to the expanded stents. Thus, it is preferred if the inventive polymer tube has an inner diameter of 0.5-15 mm, further preferred of 1-10 mm, and even more preferred from 2-6 mm. From polymer stents of these diameters that correspond to the diameters of dilated stents (nominal diameter), the vascular implants are preferably laser cut. Therefore, the prepared stents are present in expanded (dilated) form.

Moreover, this is beneficial because in expanded form, the stent struts or bars point preferably in circumferential direction and thus in direction of the wound polymer filaments or respectively in direction of the molecule chains or the high strengths. Subsequently, the stents are crimped on the balloon catheter for implantation.

Thus, the present invention relates to a method for the production of a pore-free stent, preferred an resorbable pore-free stent, comprising the following steps:
a) winding or directed winding of at least one polymer filament with a diameter of ≤50 μm to a polymer tube;
b) pore-free melting of the at least one wound polymer filament; and
c) cutting of the stent from the polymer tube, preferably using laser.

A preferred method of the present invention is a method for the production of a pore-free stent, preferred an resorbable pore-free stent, comprising the following steps:
a) winding or directed winding of at least one polymer filament with a diameter of ≤50 μm to a polymer tube;
b) pore-free melting of the at least one wound polymer filament; and
c) cutting of the stent from the polymer tube, preferably using laser, wherein the diameter of the polymer tube corresponds to the nominal diameter of the stent.

Moreover, the present invention relates to a method for the production of a pore-free stent and preferably a bio-resorbable pore-free stent comprising the following steps:
a) winding or directed winding of at least one polymer filament with a diameter of ≤50 μm to a polymer tube preferably on a rotating mandrel;
b) pore-free melting of the at least one wound polymer filament, wherein the wound at least one polymer filament is pore-free melted maintaining the alignment of the molecular chains along the longitudinal axis of the filament; and
c) cutting of the stent from the polymer tube, preferably using laser.

Another aspect of the present invention relates to a method for the production of a pore-free stent and preferably a bio-resorbable pore-free stent comprising the following steps:
a) winding or directed winding of at least one polymer filament with a diameter of ≤50 μm to a polymer tube preferably on a rotating mandrel;
b) pore-free melting of the at least one wound polymer filament under vacuum; and
c) cutting of the stent from the polymer tube, preferably using laser.

Another aspect of the present invention relates to a method for the production of a pore-free stent and preferably a bio-resorbable pore-free stent comprising the following steps:

a) winding or directed winding of at least one polymer filament with a diameter of ≤50 μm to a polymer tube preferably on a rotating mandrel;
b) pore-free melting of the at least one wound polymer filament under vacuum at a temperature within the melting range or up to 15° C. above the melting range of the polymer or the wound polymer filament; and
c) cutting of the stent from the polymer tube, preferably using laser.

All herein made statements concerning preferred embodiments of an inventive method for the preparation of a polymer tube also apply to the methods for the production of the stent.

This method for the stent production in the expanded form has the additional advantage that undesired creeping of the polymers is largely prevented. Deformed polymers tend to creep back to their original form. A stent that is produced in the unstretched (crimped) form and is stretched afterwards tends to creep in direction of its original, smaller diameter. This is detrimental to stent implantation since the implanted stent reduces its diameter in the blood vessel again. This behavior is observed in the presently approved bio-resorbable stents.

However, if the stent is cut from a polymer tube with a large tube diameter that corresponds to the dilated blood vessel diameter this diameter is maintained after dilatation in the blood vessel. According to the invention, it is preferred if the stent is cut from an inventive polymer tube using laser. It is further preferred if the inventive polymer tube has a diameter that corresponds to the diameter of the dilated (or expanded or inflated) stent. The inner diameter of the expanded stent corresponds to the inner diameter of the inventive polymer tube, which is used for the production. The same holds true for the outer diameter, unless the stent is provided with a coating, e.g. an active-substance releasing coating, after production.

Another advantage of the production of the stents from tubes whose diameter corresponds to the expanded diameter, i.e. the nominal diameter, of the stents is that the danger of breakage due to overstretching above the nominal diameter is less critical than in stents that are produced from smaller tube diameters (often corresponding to the crimped, deflated stent). Since the strength of the polymer tubes from prior art was optimized at the expense of a reduced elasticity, the stents produced from smaller tube diameters are only limitedly elastic and an overstretching leads quickly to breakage. In the case of the stents produced according to the invention, greater vascular diameters are accessible at the same, limited elasticity.

Moreover, it is possible to adjust the inventive polymer tubes even more purposefully to the mechanical requirements of vascular implants:

During winding of the polymer filament, a fast rotating mandrel is moved back and forth in such a fashion that the filament is wound e.g. crosswise or under a certain angle. The crosswise or layer-wise winding of one or several polymer filaments can also take place by deflection of the filaments in an electric field especially during electrospinning.

The directed winding can happen purposefully in respect to the later strains (directions of the tensile strains) of the single bars or struts of the stent after implantation e.g. in a blood vessel. The filaments should preferably be aligned towards the direction of the highest strength strains. Further, it is possible to wind the filaments layer-wise i.e. in layers with different angles and thus to obtain the desired strengths. It is also possible to realize different tube wall thicknesses in axial direction of the tube that account for the different strength requirements of a stent, for example, in the middle or at the ends. To this end, the winding strength i.e. the number of windings of the filament is varied along the longitudinal axis on the mandrel.

Another preferred method for the preparation of a polymer tube according to the present invention comprises a step a) during which the polymer filament is wound purposefully layer-wise or crosswise under a defined angle.

Thus, for the production of a pore-free polymer tube and preferred a bio-resorbable pore-free polymer tube, a preferred method results comprising the following steps:
a) winding or directed winding of at least one polymer filament with a diameter of ≤50 μm to a polymer tube preferably on a rotating mandrel, wherein the mandrel is moved back and forth in such a fashion that the polymer filament is wound under a certain angle crosswise or layer-wise;
b) pore-free melting of the at least one wound polymer filament.

Another preferred method for the production of a pore-free polymer tube and preferred a bio-resorbable polymer tube comprises the following steps:
a) winding or directed winding of at least one polymer filament with a diameter of ≤50 μm to a polymer tube preferably on a rotating mandrel, wherein the mandrel is moved back and forth in such a fashion that the polymer filament is wound according to a specified pattern;
b) pore-free melting of the at least one wound polymer filament.

Wherein it is preferred that the pattern is chosen according to the stent design and is, for example, spiral.

Another preferred method for the production of a pore-free polymer tube and preferred a bio-resorbable polymer tube comprises the following steps:
a) winding or directed winding of at least one polymer filament with a diameter of ≤50 μm to a polymer tube, wherein the at least one polymer filament is wound in at least two layers with different angles;
b) pore-free melting of the at least one wound polymer filament.

Therein, it is especially preferred if the angles are chosen corresponding to the strength requirements of the parts produced from the tubes. In the case of a stent, these are above all radial forces that act in the single stent struts. Thus, it is of particular advantage that the angles can be chosen freely according to the stent design.

It is preferred if the winding strength i.e. the number of winding or layers of the filament on top of each other are in between 5 windings and 1000 windings in the inventive polymers, further preferred between 10 windings and 600 windings, further preferred between 25 and 500 windings and even further preferred between 50 and 300 windings.

The winding of the thin polymer filaments requires high deposition velocities i.e. high rotational velocities of the winding rotating mandrel. If the filament is wound under an angle, for example, crosswise, fast back and forth movements, i.e. high axial velocities of the mandrel are required.

In an additional preferred method for the preparation of a polymer tube according to the present invention, active agents are introduced in step a) during winding of the filaments. Preferred are active agents that be used for a reduction of a restenosis. Suitable active agents are especially anti-proliferative or anti-restenotic active agents.

The at least one used anti-proliferative or anti-restenotic active agent is preferred selected from a group comprising or consisting of: paclitaxel, rapamycin, and their derivatives such as 6-α-hydroxy-paclitaxel, baccatin or other taxoteres, biolimus A9, myolimus, novolimus, pimecrolimus, tacrolimus, temsirolimus, zotarolimus, everolimus, ridaforolimus or other so-called "taxanes" or "limus" derivatives, respectively.

Combinations of active agents can also be introduced. The active agents can exist in different concentrations. The concentration of a used active agent can also vary between different sections of the inventive polymer tube and thus the stents producible thereof. This way, in the region of the ends of the polymer tube more active agent can be present than in the middle region. Alternatively, there can be introduced a different active agent in the luminal (blood side) tube inside than on the abluminal (vessel side) tube outside. Conceivable are an active agent to promote the endothelialization on the luminal tube inside and an active agent for proliferation inhibition on the abluminal tube outside.

During layer-wise winding of solution-spun or melting-spun polymer filaments, the active agents can be applied between the polymer filaments. Thus, it is possible to integrate the active agents directly into the wall of the polymer tube. The polymer filament can, for example, before winding be impregnated with a solution of the active agent. A special possibility for the inclusion of active agents arises in solution spinning. During solution spinning, the preferably resorbable polymer is solved in a solvent usually at room temperature. The active agent can be introduced in this solution provided that it is compatible with the solvent. Thus, the active agent is already in the solution-spun filament that is wound to a tube.

During subsequent melting (baking) of the polymer tubes, the temperatures are substantially lower and thus more gentle for the active agent than during extrusion or injection moulding. During extrusion or injection moulding of the polymer tubes, the melting temperatures of the polymers are considerably exceeded.

Also, a gradient of the active agent over the wall thickness of the polymer tube can be beneficial. To this end, for example, polymer filaments with different concentrations of active agents or different active agents can be used for the preparation of the polymer tubes. Alternatively, different concentrations of active agent or different active agents can be added to a continuous polymer filament during its preparation. In combination with at least one active agent or the combination of active agents additional substances like transport mediators can be introduced.

Suitable solvents are preferred organic solvents such as chloroform (trichloromethane), methylene chloride (dichloromethane), tetrafluoroethylene (TFE), hexafluoroisopropanol (HFIP), tetrahydrofuran (THF), acetone (dimethyl ketone), diethyl ether, methanol, ethanol, propanol, isopropanol, diethyl ketone, dimethylformamide (DMF), dimethylacetamide, acetic acid ethyl ester, dimethyl sulfoxide (DMSO), benzene, toluene, xylene, t-butyl methyl ether (MTBE), cyclohexane, N-methyl-2-pyrrolidone, pentane, hexane, heptane, wherein methylene chloride and chloroform are preferred.

The subsequent release of the active agents occurs with implantation of the polymer tubes or the implants such as stents produced thereof. In the initial phase after implantation of stents, produced from the inventive polymer tubes, degradation processes of the polymer molecules occur without degradation of the stent i.e. without loss of mass. The release of the active agent essentially occurs by diffusion. In the later commencing degradation, the release of the active agent takes place by erosion. It is also possible to introduce the active agents in different concentrations in the tube wall to thus account for the course of diffusion and the degradation of the stent and/or the healing process of the blood vessel. By contrast, in coated resorbable and non-resorbable polymer stents, first the active agent coating is degraded and only afterwards the stent without active agent being present.

Still, it is also possible to furnish the inventive polymer tubes or polymer stents with an additional coating. This coating is preferred a coating releasing active agent(s). The active agent or the combination of active agents can be applied on the surface of the tubes or stents alone or in a suitable matrix. A suitable matrix can be a polymer, preferred an resorbable polymer. The polymer of the coating releasing active agent(s) may be identical with the polymer of the backbone.

Together with the active agent, other substances can be applied that influence the release from or the adhesion to the stent of the active agent. Pharmaceutically acceptable carrier in a coating releasing active agent(s) can be substances selected from a group, consisting of or comprising: starch, sodium carboxymethyl starch, sorbitol, sucrose, magnesium stearate, dicalcium phosphate, calcium sulfate, talcum, mannitol, polyvinyl alcohol, polyvinyl pyrrolidone, gelatin, natural sugars, both natural and synthetic rubber such as acacia gum, guar gum, sodium alginate, sodium benzoate, sodium acetate, glycerides, isopropyl myristates, and -palmitate, citrate such as tributyl and triethyl citrates and acetyl derivatives thereof, phthalates such as dimethyl phthalate or dibutyl phthalate, benzyl benzoate, triacetin, 2-pyrrolidone, agar, cellulose, cellulose derivatives such as methyl cellulose, sodium carboxymethyl cellulose and hydroxypropylmethyl cellulose.

The coating releasing active agent(s) can be applied on the backbone (consisting of stent struts that were cut from the inventive polymer tube) using known methods such as spray methods, immersion methods, plasma methods, brush methods, syringe methods, electrospinning, or pipetting methods.

It becomes evident from the above explanations that the properties of the inventive polymer tubes are also properties of the stents or vascular supports produced from these tubes. Thus, all herein disclosed features and combinations of features of the inventive polymer tubes are also understood in respect to the inventive stents. Both the polymer tubes and the stents are characterized mainly by the inventive production methods. Hence, the present invention also relates to polymer tubes and stents obtainable by one of the inventive methods. The polymer tubes and stents produced using one of the inventive methods are distinguished by their improved radial strength while at the same time high or even improved elongation at break wherein the radial strength is preferred >80 MPa, more preferred >90 MPa, and even more preferred >100 MPa and the elongation at break is >30%, more preferred >40%, even more preferred >50%.

DESCRIPTION OF THE FIGURES

FIG. 1.

Curves 1, 2: Stress-strain diagram of a PLLA tube (3.3× 0.15 mm) produced according to the invention example 6 and tested with described spirals (s. FIG. 4) to determine radial tension. Curve 1 and 2 are each one test specimen, respectively.

Curve 3, 4: Stress-strain diagram of a directional PLLA tube (3.4×0.15 mm) from the state of the art of the market leader for extruded tubes for medical applications. Tested with described spirals to determine radial tension. Curve 3 and 4 are each one test specimen, respectively.

Curve 5: Stress-strain diagram of a directional PLLA tube (3.4×0.15 mm) from the state of the art of the market leader for extruded tubes for medical applications. Tested with described stripes to determine axial tension.

Curve 6, 7: Stress-strain diagram of a directional PLLA tube (3.3×0.15 mm) produced according to the invention tested with described stripes to determine axial tension. Curve 6 and 7 are each one test specimen, respectively.

FIG. 2.

Curve 1, 2: stress-strain diagrams of a PCL tube (3.3×0.15 mm) prepared according to the invention and tested with the described spirals to determine radial tensions. Curve 1 and 2 are each one test specimen, respectively Curve 3, 4: stress-strain diagrams of a PCL tube (3.0×0.15 mm) prepared according to the invention and tested with the described stripes to determine axial tensions. Curve 3 and 4 are each one test specimen, respectively Curve 5: stress-strain diagrams of a PCL tube (3.4×0.15 mm) from the state of the art of the market leader for extruded tubes for medical applications. Tested with the described stripes.

FIG. 3: Shows the experimental setup for the tensile tests according to FIGS. 1 and 2. The traverse is driven over the spindle stroke upwards. The stretching of the specimen causes a force that is measured using the calibrated load cell.

EXAMPLES

Example 1

Preparation of an Inventive Polymer Tube

An inventive polymer tube was prepared by solving the highly pure polymer raw material polycarpolactone (PCL) in tetraflouroethylene (TFE) namely 170 mg PCL per 1 mL TFE and drawn to an about 2 μm thin filament using the electrospinning method. The filament is drawn from the electrospinning nozzle with a high velocity of about 700 m/min. This process is conducted with a conveyed polymer volume of 10 mL/h at a current of 25 kV. The tetrafluoroethylene is evaporated instantly from the very thin filament that is wound on a rotating mandrel. Therein, the mandrel is moved back and forth to achieve a uniform winding i.e. a uniform layer-wise winding strength.

Subsequently, the closely juxtaposed filaments of the polymer tube are melted at a temperature above the melting temperature at about 65° C. To ensure a pore-free melting and a high density of the tube wall, a mechanical force is applied from outside on the tube i.e. the tube is pressed onto the mandrel.

Example 2

Production of an Inventive Stent

After cooling, the tube prepared according to example 1 is pulled from the mandrel and inserted into a laser system. The stent design is cut into the polymer tube using an ultrashort pulse laser. The cuttings fall out such that the stent structure consisting of the single stent struts remains. After cleaning steps, the stent is ready to be crimped onto a balloon catheter and to be implanted thereafter.

Example 3

Preparation of an Inventive Polymer Tube Containing Paclitaxel

If the stent is to release active agents to improve the healing progress, the active agent may, for example, be introduced directly into the polymer tube during preparation.

To this end, paclitaxel is mixed into the tetrafluoroethlyne solution of the polymer from example 1 in two different concentrations (1:10 and 1:3 paclitaxel to polymer). Since the polymer tube should contain two different concentrations of active agent layer-wise over the tube wall thickness, first an about 0.75 μm thin filament is drawn using the first solution in the electrospinning method and this filament is wound with high velocity on the rotating mandrel. Meanwhile, the mandrel is moved back and forth to achieve a uniform winding. After 200 layers, the winding of the filament is interrupted and continued with a filament of the second solution until 300 layers in total are wound. The method of filament melting was not changed compared to example 1. Also, the method of laser cutting of the stent as described in example 2 is not changed by the active agent.

If the concentration of active agent is to change along the tube length, filaments with differential concentrations of active agents can be incorporated as well.

Example 4

Preparation of an Inventive Polymer Tube Containing Paclitaxel

An inventive polymer tube was prepared by solving the highly pure polymer raw material polyglycolide (PGA) in hexafluoroisopropanol (HFIP) namely 80 mg PGA per 1 mL HFIP and drawn to 1 μm thin filament using electrospinning. The filament is drawn from the electrospinning nozzle with a high velocity of about 800 m/min. The hexafluoroisopropanol is evaporated instantly from the very thin filament that is wound on a rotating mandrel. Therein, the mandrel is moved back and forth to achieve a uniform winding i.e. a uniform layer-wise winding strength. This process is conducted for about 30 min with a conveyed polymer volume of 10 mL/h. For functionalization, the polymer tube is loaded with active agent during this process. To this end, the mandrel is sprayed with sirolimus towards the end of the process, after 20 minutes, after 25 minutes, and after 28 minutes. The concentration is increased by 20% in each step to obtain a high concentration in the uppermost layer and to release a decreasing concentration in the later elution time.

Afterwards, the closely juxtaposed filaments of the polymer tube are melted at a temperature above the melting temperature at about 235° C. To ensure a pore-free melting and a high density of the tube wall, the melting process is conducted under vacuum at 10 to 500 nbar.

Example 5

Preparation of a Radiopaque Polymer Tube According to the Invention

An inventive polymer tube was prepared by solving the highly pure polymer raw material polyhydroxybutyrate (PHB) in chloroform (CHCl₃) namely 40 mg PHD per 1 mL CHCl₃. For functionalization, the polymer solution is loaded with radiopaque particles. To this end, 10 mg nanoparticles of tantalum nitride are added per mL solution. Using electrospinning, the polymer is drawn to an about 500 nm thin filament. The nanoparticles stick to the filaments and are incorporated into the fiber structure. The filament is drawn from the electrospinning nozzle with high velocities of about 750 mL/min. The chloroform evaporates instantly on the very thin filament that is wound on a mandrel. Therein, the mandrel is moved back and forth to achieve a uniform winding i.e. a uniform layer-wise winding strength. This process is conducted for about 30 min with a conveyed polymer volume of 10 mL/h.

Afterwards, the closely juxtaposed filaments of the polymer tube are melted at a temperature above the melting temperature at about 185° C. To ensure a pore-free melting and a high density of the tube wall, the melting process is conducted under vacuum at 10 to 500 nbar.

Example 6

Figure 1:
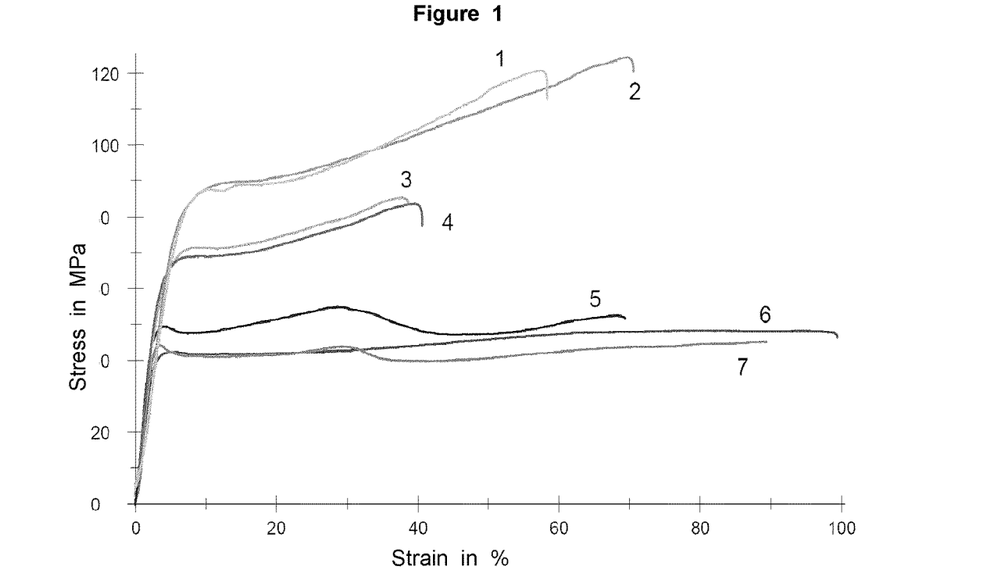
FIG. 1 shows a comparison between the stress-strain diagrams of tubes prepared from PLLA according to prior art and the inventive method.

Experimental Procedure for FIG. 1 a) Preparation of a PLLA Tube

Curve 1, 2, 6, 7: the inventive tube that was produced as follows: The highly pure polymer basic material poly-L-lactide (PLLA) is solved in chloroform (CHC₃) namely 60 mg PLLA per 1 mL chloroform and drawn into an about 0.8 µm thin filament using electrospinning. The filament is drawn from the electrospinning nozzle with high velocities of about 800 m/min. This process is conducted with a conveyed polymer volume of 8 mL/h at a current of 22 kV. The chloroform is evaporated instantly from the very thin filament that is drawn on a rotating mandrel. Therein, the mandrel is moved back and forth to achieve a uniform winding i.e. a uniform layer-wise winding strength.

Afterwards, the closely juxtaposed filaments of the polymer tube are melted at a temperature above the melting temperature at about 185° C. To ensure a pore-free melting and a high density of the tube wall, the melting process is conducted under high vacuum at 30 nbar. After cooling, the prepared tube is pulled off the mandrel.

Curve 3, 4, 5 are of a commercially available PLLA tube prepared according to the following procedure:

The PLLA tube were prepared according to prior art. To this end, a HAAKE MiniLab II Micro Compounder from ThermoFisher Scientific was loaded with previously dried PLLA granules PL38 from Purac. Extrusion was performed according to the manufacturer's standards. The extruded tube were inspected visually and cut by laser into pieces of 300 mm each. These tube pieces were introduced into a balloon form machine 503 of the BW-Tec AG with a shape of an inner diameter of 3.4 mm and a length of 140 mm. Then, the tubes were impinged with 12 bar and the form was heated to a temperature 30° C. above the glass transition temperature. Subsequently, the tubes were removed from the form and again inspected visually.

Figure 4:
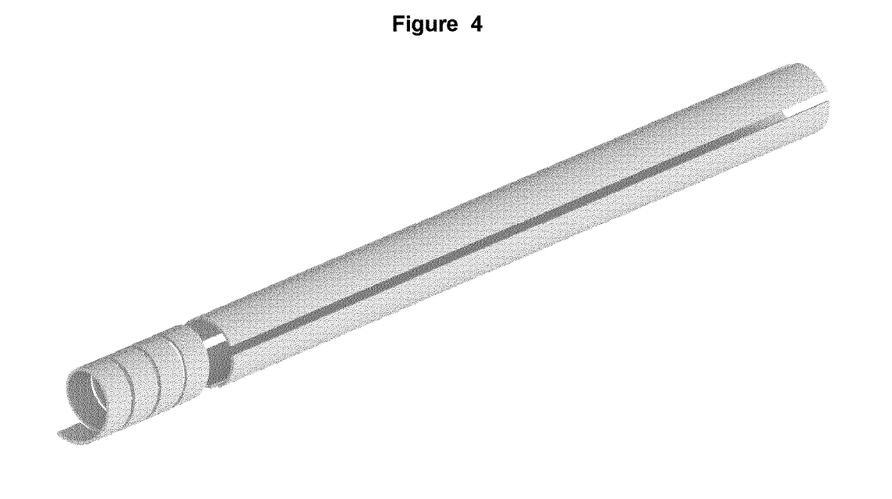
FIG. 4: Shows how the polymer tubes are cut with the laser to obtain tube pieces for the tensile tests according to FIGS. 1 and 2. These specimen are used for oriented as well as anisotropic polymers such that tensions in both radial and axial direction can be recorded.

Both tubes, i.e. the inventive and the prior art, were inserted into the collet chuck of a laser system. Using an ultrashort pulse laser, the specimen design (FIG. 4) is cut into the polymer tube to be tested. The cuttings fall out such that only the specimen remains. The stripe (see FIG. 4, right part) serves to test the mechanical properties in axial direction. The spiral is used for testing in radial direction (see FIG. 4, left part). The spiral does not run along radial direction completely but has a slight slope. This slope, however, can be neglected in the determination of the radial force because the resulting inaccuracy is below 1% and because the slope leads rather to an under estimation than an overestimation of the tension. The stripes have an uniform width of 2 mm and a length of 4 mm. The thickness of the stripes corresponds to the thickness of the initial tube. The specimen are controlled under the light microscope, numbered and immediately after laser cutting, the tensile test is conducted.

b) Conduction of Tensile Tests for the Curves

Figure 3:
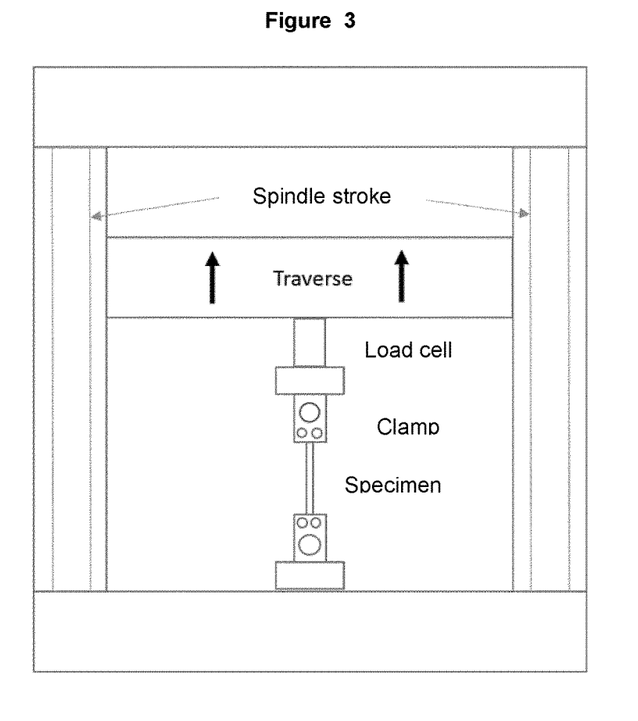

The tensile tests are conducted at room temperature between 20° C. and 25° C. The generated specimens are inserted into a tensile test machine Zwick Z005 using flat mechanical clamping claws. The stripes are already present in a flat form such that they are pushed between the clamping claws and the upper claw can be fixated using two clamp screws. Then, the traverse is moved downwards until the sample can be pushed into the lower clamping claw. Again, the clamping claw is closed using two clamp screws. The spirals are drawn in the same way as the stripes, however, they have to be straightened before. For this purpose, an end of the spiral is inserted into the upper mount and wound up and disentangled using tweezers and pushed into the lower mount. During the tensile test, a prestress of 5 MPa is applied to straighten the sample. Subsequently, the respective sample is pulled apart with a constant velocity of 5 mm/min. A calibrated load cell with a maximal force of 5 kN measures the resulting force. In the accompanying software, the force is divided by the initial cross section and thus the tension, as shown in FIG. 1, calculated. The elongation of the x axis is determined by the travel of the traverse. The experimental setup is shown in FIG. 3.

Example 7

Experimental Procedure for FIG. 2

A tube is prepared according to example 1. Another commonly extruded tube (FIG. 2, curve 5) was produced in the same way as the commercially available tubes. To this end, a HAAKE MiniLab II Micro Compounder from the company ThermoFisher Scientific was loaded with previously dried PLC granules PC12 from the company Purac. Extrusion was performed according to the manufacturer's standards. The extruded tube were inspected visually and cut by laser into pieces of 300 mm each. These tube pieces were introduced into a balloon form machine 503 of the BW-Tec AG with a shape of an inner diameter of 3.4 mm and a length of 140 mm. Then, the tubes were impinged with 12 bar. Subsequently, the tubes were removed from the form and again inspected visually.

The tubes, i.e. the inventive and prior art, were tested as in example 6. Since the common tube is isotropic, both specimens from the common tube result in the same results and thus only one curve is shown.

Example 8

Preparation of an Inventive Hybrid-Polymer Tube

The inventive hybrid-polymer tube was prepared as follows: The highly pure polycaprolactone (PCL) is solved in tetrafluoroethylene (TFE) namely 170 mg PCL per 1 mL TFE. Another highly pure, high-molecular weight polymer (PLLA) is solved in chloroform namely 60 mg PLLA per 1 mL chloroform. Using electrospinning, the PCL is drawn to an about 1 µm thin filament. The filament is drawn from the electrospinning nozzle with a high velocity of about 800 m/min. The TFE is evaporated instantly from the very thin filament that is wound on a rotating mandrel. Therein, the mandrel is moved back and forth to achieve a uniform winding i.e. a uniform layer-wise winding strength. After 10 layers of filaments on top of each other, the mandrel is inserted into a second electrospinning installation. In the second electrospinning process, the PLLA is drawn to an about 700 nm thin filament. The filament is also drawn from the electrospinning nozzle with a high velocity of about 800 m/min. The chloroform is evaporated instantly from the very thin filament that is wound on a rotating mandrel. Therein, the mandrel is moved back and forth to achieve a uniform winding i.e. a uniform layer-wise winding strength. Again, 10 layers of filaments are produced. The sequence of the first two electrospinning is repeated 15 times, wherein the first and the last layer always consist of the polymer with the lower melting point, in this case PCL.

Subsequently, the closely juxtaposed filaments of the polymer tube are melted at a temperature above the melting temperature PCL. Thus, the PCL filaments are melted pore-free with each other. To ensure a pore-free melting and a high density of the tube wall, the melting process is conducted under vacuum at 10 to 500 nbar. The PLLA filaments are not melted at 70° C. and remain as filaments. Thus, the high strength known for filaments is exploited. By means of the vacuum, the filaments a pressed against each other as strong as possible such that the free non-load-carrying volume is reduced. The filaments are kept in place by the layers of PCL and ensure that the tube is not falling apart during subsequent laser cutting. From this hybrid tube, stents can be cut that are implantable with common balloon catheters. The PLLA filaments provide for a high radial strength whereas the pore-free layers of PCL take on the loads in axial direction. Because PCL is in the glass state at body temperature, there is great potential for deformation that has in turn a positive effect on axial bending capacity (also called conformability). This means that the stent keeps the artery open but does not straighten it unnecessarily.

The invention claimed is:

1. A method for a preparation of a pore-free polymer tube comprising:
   a. directed winding of at least one polymer filament with a diameter of ≤50 μm to form a polymer tube; and
   b. pore-free melting of the at least one polymer filament in the polymer tube at a melting point of the at least one polymer filament or up to a maximal 15° C. above the melting point of the at least one polymer filament under vacuum for 5 seconds to 180 seconds to form the pore-free polymer tube.

2. The method for the preparation of a pore-free polymer tube according to claim 1, wherein the at least one polymer filament is prepared by solution spinning, electrospinning, or melting spinning.

3. The method for the preparation of a pore-free polymer tube according to claim 1, wherein in step a) the at least one polymer filament is wound on a rotating mandrel.

4. The method for the preparation of a pore-free polymer tube according to claim 1, wherein the polymer tube has a nominal diameter, wherein the nominal diameter is an inner diameter of the polymer tube after dilatation.

5. The method for the preparation of a pore-free polymer tube according to claim 1, wherein the at least one polymer filament is wound directionally.

6. A method for the preparation of a hybrid polymer tube comprising:
   a. winding at least one polymer filament of a polymer A with a diameter of ≤50 μm, thereby forming a first layer of polymer tube; and
   b. winding at least one polymer filament of a polymer B with a diameter of ≤50 μm on top of the first layer of polymer tube, thereby forming a second layer of polymer tube; and
   c. winding at least one polymer filament of polymer A with a diameter of ≤50 μm on top of the second layer of polymer tube, thereby forming a third layer of polymer tube;
   d. optionally repeating steps b) and c) multiple times; and
   e. melting or pore-free melting at least the first and the third layer of polymer tube at a temperature at or above the melting point of polymer A but at or below the melting point of polymer B, wherein the melting point of polymer B is at least 10° C. higher than the melting point of polymer A.

7. The method for the preparation of a pore-free polymer tube according to claim 3, wherein the velocity of the rotating mandrel is at least 10,000 rpm.

* * * * *